United States Patent [19]

Robinson

[11] Patent Number: 5,573,020
[45] Date of Patent: Nov. 12, 1996

[54] DENTAL FLOSSING DEVICE AND METHOD THEREFOR

[76] Inventor: Dane Q. Robinson, 6015 E. Quartz Mountain Rd., Paradise Valley, Ariz. 85253

[21] Appl. No.: 93,188

[22] Filed: Jul. 16, 1993

Related U.S. Application Data

[63] Continuation-in-part of Ser. No. 1,521, Jan. 7, 1993, abandoned.

[51] Int. Cl.⁶ .................................................. A61C 15/00
[52] U.S. Cl. ........................ 132/322; 433/118; 433/143
[58] Field of Search ...................... 132/321, 322, 132/323, 324; 433/82, 118, 142, 143; 601/139, 141, 142, 162

[56] References Cited

U.S. PATENT DOCUMENTS

| | | |
|---|---|---|
| Re. 30,536 | 3/1981 | Perdreaux, Jr. . |
| 3,563,233 | 2/1971 | Bodine . |
| 3,809,977 | 5/1974 | Balamuth et al. . |
| 3,902,510 | 9/1975 | Roth ........................................ 132/322 |
| 3,967,617 | 7/1976 | Krolik . |
| 4,004,344 | 1/1977 | Gold et al. . |
| 4,019,522 | 4/1977 | Elbreder ................................. 132/322 |
| 4,048,723 | 9/1977 | Thorup ..................................... 433/82 |
| 4,205,664 | 6/1980 | Baccialon . |
| 4,235,253 | 11/1980 | Moore . |
| 4,319,595 | 3/1982 | Ulrich ..................................... 132/322 |
| 4,326,547 | 4/1982 | Verplank . |
| 4,347,839 | 9/1982 | Youngclaus, Jr. . |
| 4,608,019 | 8/1986 | Kumabe et al. ........................ 433/119 |
| 4,820,154 | 4/1989 | Ludwig et al. . |
| 4,913,133 | 4/1990 | Tichy . |
| 4,995,403 | 2/1991 | Beckman et al. ....................... 433/118 |
| 5,002,487 | 3/1991 | Tichy ...................................... 433/118 |
| 5,050,625 | 9/1991 | Siekmann ............................... 132/323 |
| 5,071,348 | 12/1991 | Woog . |
| 5,100,321 | 3/1992 | Coss et al. .............................. 433/118 |
| 5,123,841 | 6/1992 | Millner ................................... 132/322 |
| 5,224,500 | 7/1993 | Stella . |
| 5,236,358 | 8/1993 | Sieffert .................................. 433/102 |
| 5,293,886 | 3/1994 | Czapor ................................... 132/329 |

FOREIGN PATENT DOCUMENTS

| | | |
|---|---|---|
| 0354352 | 7/1989 | European Pat. Off. . |
| 4226659A1 | 2/1994 | Germany . |

*Primary Examiner*—Todd E. Manahan
*Attorney, Agent, or Firm*—Seed & Berry LLP

[57] ABSTRACT

An electro-mechanical dental flossing device is disclosed for flossing the area between a portion of the tooth and the gum tissue. The device comprises an elongated member coupled to a motor source to effect oscillation of the elongated member. The elongated member includes an intermediate portion and a tip which are capable of being received between the tooth and the gum tissue.

56 Claims, 3 Drawing Sheets

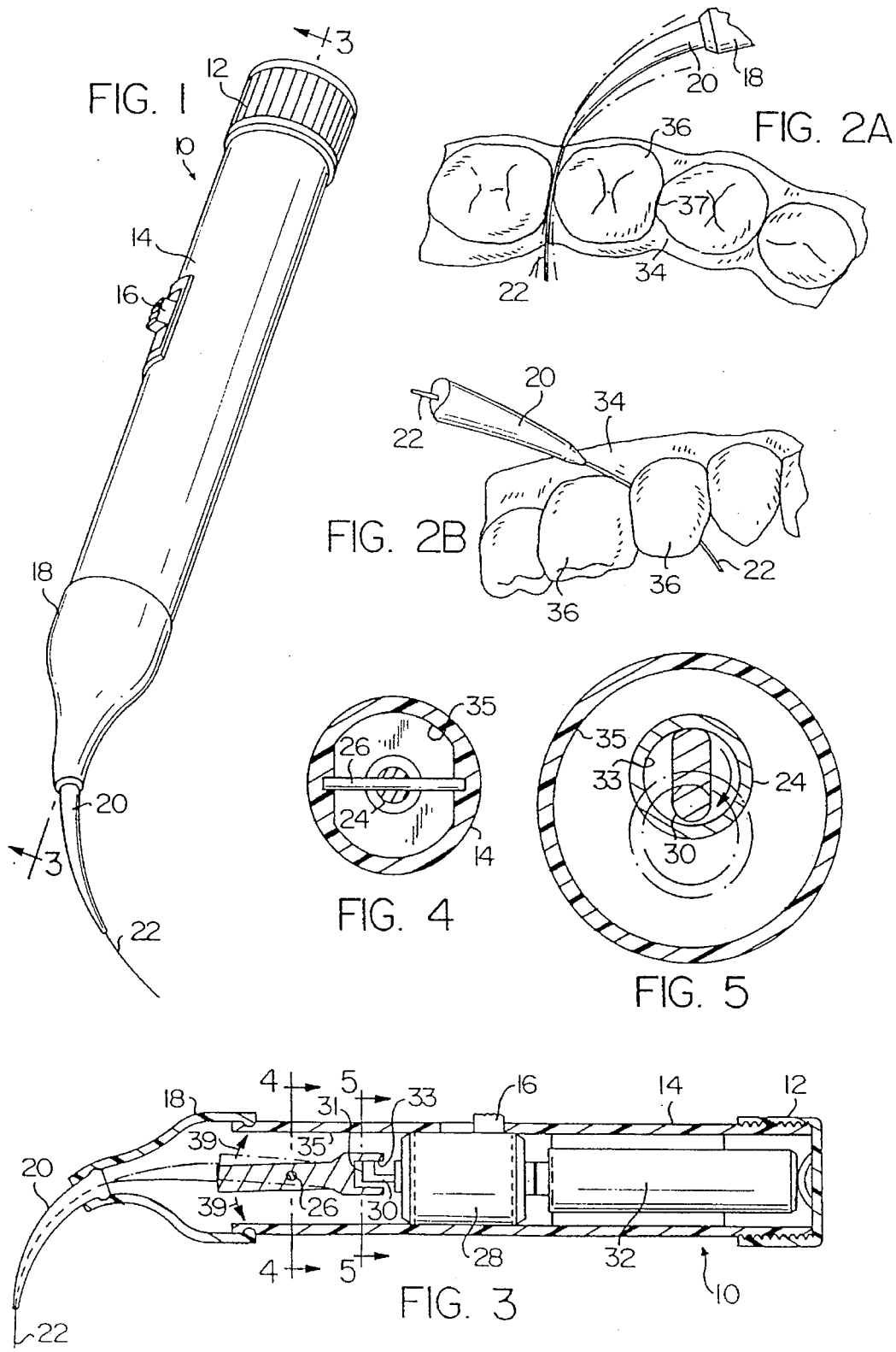

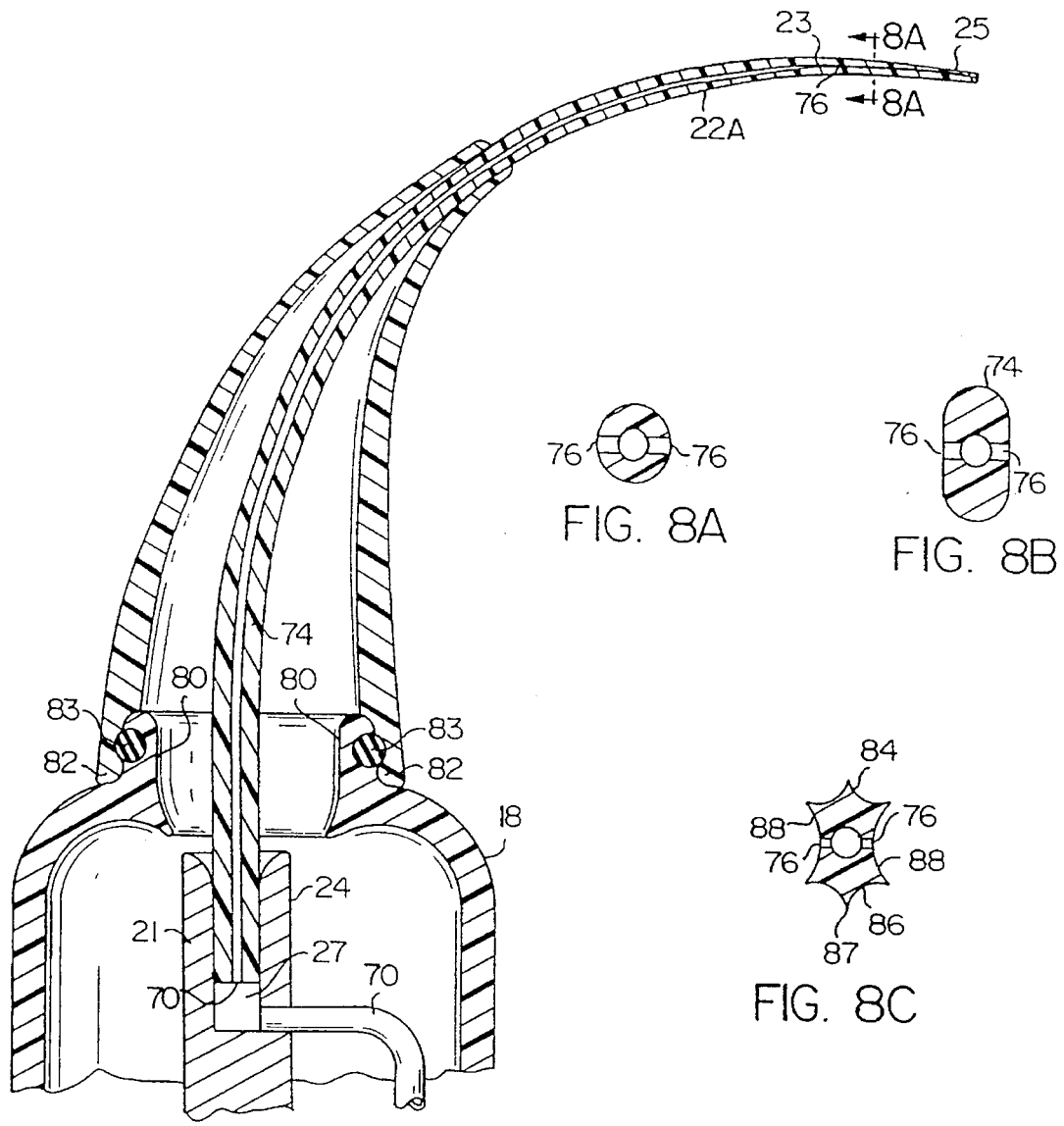
FIG. 7
FIG. 8A
FIG. 8B
FIG. 8C
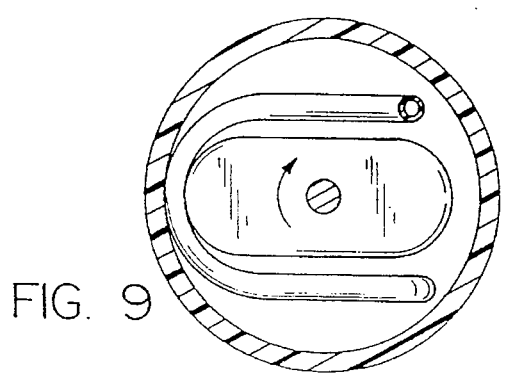
FIG. 9

DENTAL FLOSSING DEVICE AND METHOD THEREFOR

CROSS-REFERENCE TO RELATED APPLICATION

This application is a continuation in part of applicant's U.S. Ser. No. 08/001,521, filed Jan. 7, 1993, now abandoned.

FIELD OF INVENTION

This invention generally relates to dental devices and methods, and, more specifically, to an electro-mechanical dental flossing device and method therefor which provides a hand held, electrically powered flossing tool having a tip comprised of a substantially thin, flexible member capable of being received between a tooth and the adjacent interdental papilla portion of the gum (the dental sulcus). The tip is oscillated to produce a flossing action.

DESCRIPTION OF PRIOR ART

The prior art provided various types of dental devices and methods for the cleaning of teeth as well as the massaging of the gum tissue. For example, U.S. Pat. No. Re. 30,536, "Ultrasonic Device and Method", issued on Mar. 3, 1981 shows an apparatus which utilizes an ultrasonically driven head in conjunction with a spray of liquid or slurry containing abrasive material to operate as a cutting or cleaning tool in dental operations. As a second example, U.S. Pat. No. 4,913,133, "Hand Held Periodontic Tool", issued on Apr. 3, 1990 discloses a hand held periodontic tool which vibrates a flexible tip for use in massaging gum tissue, but which cannot be used for dental flossing. Such prior art devices, however, are typically unable to reach the area between the portion of the tooth located beneath the gum tissue surface and the gum tissue itself (interdental papilla). This area was generally cleaned with dental floss.

However, the use of dental floss can be somewhat cumbersome. In many instances there are contact areas between the teeth (i.e. portions of the crowns of the teeth are closely adjacent or touching), typically at the top of the crown. In order for floss to be received between the teeth, it is generally necessary for the floss to be forced between the teeth from above, and must pass through any contact area. However, such contact areas often do not provide adequate space to permit passage of the floss. This tends to result in the floss shredding or breaking rather than passing between the teeth. In such instances, some manner of threading device must be employed.

Devices which dispose a strand of floss between rigid arms of a forked or "U" shaped tip to facilitate flossing are available. Electrical flossing devices which reciprocate such a tip are also known. An example of such a device is described in U.S. Pat. No. 4,235,253, issued Nov. 25, 1980, to D. A. Moore.

Thus, although the prior art discloses a variety of devices for the cleaning of the exposed surfaces of the teeth and for the massaging of the gum tissue, and devices to facilitate flossing, there remains a need for a device to more effectively and efficiently clean or floss the area not only between the teeth, but also the area between the interdental papilla and the interproximal surface of the tooth.

SUMMARY OF INVENTION

The present invention provides an improved electro-mechanical dental flossing device and method therefor which effectively and efficiently provides a flossing action both between and around teeth as well as providing a flossing action between the portion of the tooth that is beneath the gum tissue surface adjacent to the interdental papilla.

In accordance with one aspect of the present invention an electro-mechanical dental flossing device employs a thin and flexible elongated member capable of being at least partly received between a tooth and the adjacent interdental papilla portion of the gum. The device employs a motive source to effect motion of the elongated member by way of a coupling.

In accordance with another aspect of the invention, the elongated member manifests a predetermined cross-section. In accordance with various aspects of the invention, the member may have: a generally circular cross-section with a diameter no greater than approximately 0.025 inch; a generally elliptical cross-section with a minor diameter no greater than approximately 0.025 inch; a cross-section generally circumscribed by a top, a bottom and inwardly concave arcuate sides when the maximum transverse distance between corresponding points of the side is no greater than approximately 0.025 inch.

In accordance with another aspect of the invention, the motive source is a motor which includes a shaft with an eccentric member mounted thereon. The coupling has a translation member connected to the elongated member and an axial aperture which receives the eccentric member. Rotation of the eccentric member causes repetitive translation of the coupling and the elongated member. Alternatively, flossing motion of the elongated member is effected by connecting the base of the elongated member directly to the motor shaft or eccentric.

In accordance with another aspect of the invention, the elongated member includes a conduit. The conduit is in communication with a fluid reservoir and with an orifice in the surface of the elongated member. A pump is disposed to propel fluid from the reservoir through the conduit to the orifice.

BRIEF DESCRIPTION OF THE DRAWING

The preferred exemplary embodiment of the present invention will hereinafter be described in conjunction with the appended drawing, wherein like designations denote like elements, and:

FIG. 1 is a perspective drawing of a first embodiment of a flossing device in accordance with this invention;

FIG. 2A is an elevational view showing the elongated member of the device of FIG. 1 flossing the area between two teeth;

FIG. 2B is front perspective view showing the elongated member of the device of FIG. 1 flossing the area between a portion of a tooth that is beneath the gum tissue surface and the gum tissue itself;

FIG. 3 is a cross sectional view of the flossing device of FIG. 1 taken along the line 3—3 of FIG. 1;

FIG. 4 is a cross sectional view of device of FIG. 1 and taken along the line 4—4 of FIG. 3;

FIG. 5 is a cross sectional view of the device of FIG. 1 taken along the line 5—5 of FIG. 3;

FIG. 7 is an expanded view of the tip of the device of FIG. 6;

FIGS. 8A–C are cross sectional views of various embodiments of an elongated member taken along line 8—8 of FIG. 7; and FIG. 9 is a cross-sectional view of the device of FIG. 6 taken along line 9—9 showing a preferred embodiment of a pump.

DESCRIPTION OF THE PREFERRED EMBODIMENT

Figure 3A:
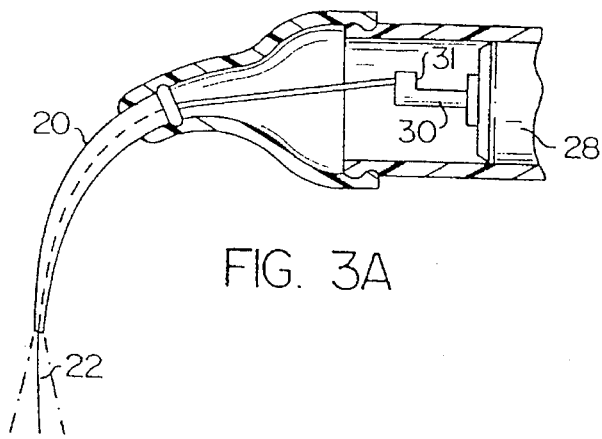
FIG. 3A is a partial cross sectional view of an alternative embodiment of a mechanism for effecting motion of the elongated element in a flossing device in accordance with the present invention.

Referring to FIGS. 1 and 3, an electro-mechanical dental flossing device 10 in accordance with the present invention suitably comprises a lower cap 12, a case 14, a generally conical tip 18, enclosing a power source 32 (e.g. battery), a motor 28, a switch 16, an elongated member 22, and a mechanism coupling member 22 to motor 28. The coupling mechanism suitably includes a translation member 24 pivotally mounted within case 14. Lower cap 12 is removably fixed to one end of case 14. Electrical control switch 16 extends through the sidewall of case 14. Conical tip 18, suitably formed of a resilient material such as a polymer or rubber composition, is attached, preferably removably, to the opposite end of flossing device case 14. Elongated member 22 extends through a rubber insert 20, which is disposed within tip 18 as shown in FIG. 3.

Elongated member 22 includes a base portion 21, an intermediate portion 23 and a tip portion 25. As will be more fully discussed, at least intermediate portion 23, and preferably also tip portion 25 are configured to be between the teeth and the interdental papilla. Elongated member 22 can be made of any material suitable for use in the human mouth which is flexible and resilient. Suitable materials can include plastics, metal wire, textiles and the like which are flexible, have a memory and are impregnable to the environment of the mouth. For example, elongated member 22 may comprise a Nickel-Titanium alloy wire, having a diameter on the order of about 0.010 inches to about 0.025 inches. In some cases, a protective coating of plastic or other insulator, such as, but not limited to, TEFLON™ may also be employed.

If desired, elongated member 22, or a protective coating, or both can be impregnated with a diffusant, such as a medicament, e.g. fluoride, a fluoride release, a germicide, or an anti-bacterial release, or a flavor, such as mint or cinnamon. As will hereafter be described, fluids such as, for example, medicaments and mouthwash, can also be applied to the user's teeth and gums through member 22A.

Referring to FIG. 3, power source 32, which is preferably a battery, is electrically coupled to electric motor 28. Motor 28 is selectively energized by power source 32 through switch 16.

Motor 28 is employed to oscillate elongated member 22. Motor 28 includes an axially protruding arm 30 which rotates when motor 28 is energized. The distal end of axial arm 30 includes an eccentric 31 (e.g. cam) disposed to penetrate an axial aperture 33 on one end of motion translation member 24. Base 21 of elongated member 22 is secured to the opposite end of translation member 24. Preferably, base 21 received in an axial bore 27 in translation member 24. Base 21 is preferably removably engaged by friction fit, or otherwise secured in bore 27. Motion translation member 24 is free to oscillate about a pin 26 which is fixedly attached to an inner wall 35 of case 14.

Flossing device 10 provides a particularly convenient mechanism for effectively and efficiently accessing not only the tooth surfaces between the teeth for cleaning and application of fluids, but also the sulcus between the interdental papilla portions of the gum and the teeth, irrespective of contact areas between the teeth. Referring to FIGS. 2A and 2B, the human mouth includes a plurality of adjacent teeth 36 disposed in the gums 34. Each tooth typically includes a crown (body) portion projecting above the gum, a root connecting the tooth to bone, and a constricted neck portion between the root and crown surrounded by the gums. In many instances, the relative dispositions of adjacent teeth 36 create contact areas 37 between the crowns of the teeth, i.e., portions of the crowns of adjacent teeth touch or nearly touch. In many such instances, contact areas make access to the sulcus between interdental papilla and the neck of the tooth from above, as conventionally required, particularly difficult, if not impossible. Tip 25 and intermediate portion 23 of elongated member 22 are dimensioned and configured to be received between teeth 36 (FIG. 2A). Intermediate portion 23 and, preferably tip 25, are also dimensioned and configured to be received in the sulcus between interdental papilla and tooth (FIG. 2B). However, elongated member 22, while resilient, is sufficiently stiff to maintain its shape, and thus is capable of being inserted into the area between teeth 36 and ultimately within the sulcus, irrespective of contact areas 37 by passing between teeth 36 from the labial (front) or lingual (back) directions below the contact areas. A flossing action is realized through motion of member 22 with member 22 situated as shown in FIGS. 2A and 2B.

Referring to FIG. 4, motion translation member 24 is fixedly attached to inner wall 35 of flossing device case 14 by pin 26. When flossing device 10 is in operation, motion translation member 24 oscillates about fixed pin 26 as shown by arrows 39 in FIG. 3.

Referring to FIG. 5, eccentric 31 on arm 30 is received within axial aperture 33 of motion translation member 24. When rotated, protective periphery of eccentric 31 effective moves about an axis that is off-set from the axial center of motion translation member 24 such that the rotation of eccentric 31 produces an oscillatory motion of motion translation member 24 about pin 26. Thus, rotation of the axial arm 30, through operating electric motor 28, causes an oscillation motion (as shown by the arrows 39) of motion translation member 24.

In operation, electric switch 16 completes the electrical circuit to energize electric motor 28 from power supply 32. If desired, switch 16 can have multiple settings for different oscillation speeds of motor 28. While operating, electric motor 28 rotates axial arm 30. The rotation of eccentric 31 by axial arm 30 within axial aperture 33 of motion translation member 24 causes the oscillatory motion of the motion translation member 24 about fixed pin 26. Due to the rapid oscillation of motion translation member 24, elongated member 22 oscillates to produce the desired flossing action between two teeth 36 or between a tooth 36 and gum portion 34.

The desired flossing motion can be imparted to elongated member 22 in numerous ways in addition to the mechanism described above. For example, as shown FIG. 3A, in an alternative embodiment, translation member 24 can be omitted and the base of member 22 can be directly connected to the distal end of motor arm 30, e.g. to eccentric 31. As a consequence of the arcuate disposition of elongated member 22 with respect to the axis of motor arm 30, and the interaction of member 22 with e.g. tip 18, rotation of arm 30 will cause member 22 to effect movement with both rotational and translatory components, e.g. to effectively precess as generally indicated in dotted line in FIG. 3A. The translatory component of such motion is of greater magnitude if the base of member 22 is attached to motor arm 30 offset from the central axis of arm 30, e.g. in the vicinity of the periphery of eccentric 31.

Figure 6:
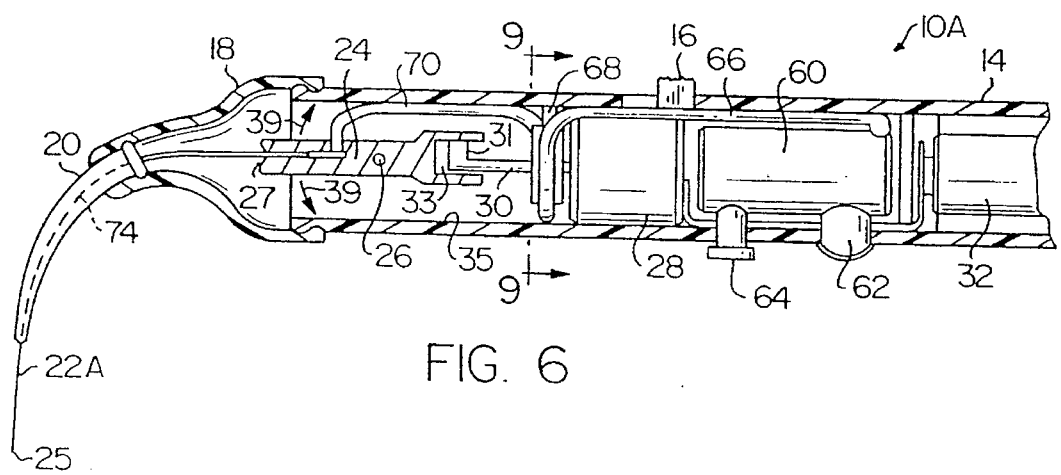
FIG. 6 is a cross section view of an alternative embodiment of the flossing device of FIG. 1 taken along line 3—3 of FIG. 1 including a fluid reservoir and a pump.

Referring now to FIG. 6, an alternative embodiment of a flossing device 10A includes provisions for applying fluids such as medicaments to the gums and teeth. Flossing device 10A suitably includes, in addition to the components previously described in conjunction with FIGS. 1 through 5, a fluid reservoir 60, a pump 68, and respective conduits 66 and 70 providing communication between reservoir 60, pump 68, and ultimately elongated member 22. As will be discussed, in this embodiment, elongated member 22 includes an axial conduit and apertures for delivering the fluid to the user's teeth and gums. Fluid reservoir 60 is suitably a collapsible polymeric bag, having a capacity of from about two to four liquid ounces. If desired, reservoir 60 can be refillable communicating with capped filling orifice 64 extending through the sidewall of casing 14. Alternatively, reservoir 60 can be disposable, removably received within casing 14 and releasably coupled to conduit 66. Fluid reservoir 60 may be any vessel capable of containing fluid and dispensing it through conduit 66. Reservoir 60 is preferably configured to be disposed within casing 14. However, if desired, conduit 66 can be channeled through the sidewall of casing 14 and cooperate with an external reservoir. In this case, reservoir 60 would be purchased prefilled with the medicament or other fluid to be applied to the user's teeth and gums, made to communicate with conduit 66 and received within casing 14. Communication with conduit 66 can be effected in any convenient manner, such as, for example, a nipple which is punctured and received within the end of conduit 66, a fixture on the end of conduit 66 which punctures a resilient portion of reservoir 60 or cooperating fittings, or the like, applying fluids such as medicaments, bactericides, germicides, fluorine treatments, mouthwash or the like to the user's teeth and gums.

If desired a level indicating mechanism can be provided. For example, reservoir 60 may be formed of a translucent or transparent material, and a window 62 provided in the side wall of casing 14.

Referring now to FIG. 6 and 7, elongated member 22A includes an axial conduit 74 communicating between a first orifice 72 in base portion 21, and at least one small orifice 76 disposed in either intermediate portion 23 or tip portion 25, as will be explained. Preferably, numerous small orifices are provided in intermediate portion 23, communicating between the sidewall of intermediate portion 23 and conduit 74.

Conduit 70 is coupled to elongated element conduit 74. The coupling may be effected by any mechanism consistent with the movement of element 22A effected by translation member 24. Preferably, as in the embodiment of FIGS. 1 through 5, base 21 of elongated member 22A is received in a friction fit in an axial bore 27 in translation member 24. Preferably, the communication is effected through translation member 24. A transverse channel 75 is formed, extending from axial bore 27 through the sidewall of member 24, and is configured to closely receive and retain the end of conduit 70. Conduit 70 is preferably formed of resilient material, and enough slack is provided to permit the desired movement of member 24 and elongated element 22a.

In operation, pump 68 draws a fluid from reservoir 60 causing it to flow through conduits 66, 70, and 74, so that it is ultimately dispensed through orifices 76 and elongated member 22a. Pump 68 may be any device suitable for effecting that function, preferably driven by motor 28. Referring to FIGS. 6 and 9, a particularly advantageous pump 68 employs a cam or eccentric 90 disposed for rotation on arm 30. A flexible conduit 92, coupling conduits 66 and 70 is disposed for cooperation with the periphery of eccentric 90. A retainer 94, suitably in the form of an annulus, may be employed to ensure proper disposition of conduit 92 relative to eccentric 90. Eccentric member 90 is suitably elliptical in shape. When rotated, the periphery of eccentric 90 in the vicinity of the long axis, partially collapses or otherwise distorts conduit 92, drawing fluid from reservoir 60 and urging the fluid in conduit 92 into conduit 70, and ultimately to orifices 76. If desired, conduits 66, 92, and 70, can be formed of a single length of resilient, e.g., polymeric, tubing.

If desired, particularly where replaceable elongated members 22, 22A are employed, tip 18 may be removably connected to casing 14 to facilitate replacement of elongated member 22, 22A. The connection is preferably water tight. Referring to FIG. 7, respective collars 80 and 82, are formed on the upper periphery of casing 14, and lower inner periphery of tip 18, respectively. The inside diameter of the base of tip 18 is slightly larger than that of collar 80. Collars 80 and 82 are resilient enough that collar 82 will snap over collar 80. In addition, a flexible O-ring 83 can be employed if desired.

Intermediate portion 23, and preferably tip 25, may manifest any cross section in accordance with the present invention so long as it may be received between the inter-dental papilla portion of the gums and an adjacent tooth. The cross section can be consistent along its length, or may vary with length. In the simplest case, as shown in FIG. 8A, a circular cross section can be employed. The diameter of the cross section is sufficiently small to be received between inter-dental papilla and tooth, e.g., no greater than about 0.025-inch. Similarly, as shown in FIG. 8B, all or a part of intermediate portion 23 may manifest an elliptical cross section having a minor diameter that is sufficiently small so that it can be received between inter-dental papilla and adjacent tooth, e.g., no greater than 0.025-inch. In each instance, axial conduit 74, and orifices 76 communicating with axial bore 74 are preferably provided.

However, more complex cross sections can be advantageously employed. For example, referring to FIG. 8C, one embodiment of intermediate portion 23 of elongated member 22a in accordance with the present invention has a cross-section circumscribed by a top 84, a bottom 86 and respective sides 88. Sides 88 are suitably arcuate, namely, inwardly directed concave arcs. Orifices 76 are situated in the narrow waist of sides 88. In accordance with the preferred embodiment, the maximum transverse distance between corresponding points on sides 84 is sufficiently small so that intermediate portion 23 can be accommodated between the interdental papilla portion of the gum and the surface of the adjacent tooth, e.g., is no greater than about 0.025 inch. Bottom 86 also suitably converges to a point 87. Thus, while the invention has been particularly shown and described with reference to the preferred embodiment thereof, it will be understood by those skilled in the art that the foregoing and other changes in form and details may be made therein without departing from the spirit and scope of the invention.

I claim:

1. Apparatus for cleaning the surfaces of teeth underlying the inter-dental papilla portion of the gums in a human mouth by effecting a flossing action, comprising:

a flexible, resilient, non-abrasive elongated member;

said elongated member including a base portion, an elongated intermediate portion of predetermined cross-sectional configuration, and a tip;

said intermediate portion and said tip being capable of being received between adjacent teeth without traversing any contact areas between the teeth from at least the front of the mouth and being capable of effecting the flossing action therebetween; and at least the intermediate portion being capable of being received in the sulcus between a tooth and the adjacent inter-dental papilla portion of the gum for effecting the flossing action therein; and a motive source; and a coupling connecting the base portion of the elongated member to the motive source to effect motion of the elongated member.

2. The apparatus of claim 1, wherein both said intermediate portion and said tip are capable of being received in the sulcus between a tooth and the adjacent interdental papilla portion of the gum for effecting the flossing action therein.

3. The apparatus of claim 1 wherein said coupling effects oscillation of the elongated member.

4. The apparatus of claim 1, wherein said intermediate portion has a generally circular cross-section and a diameter no greater than approximately 0.025 inch.

5. The apparatus of claim 1, wherein said intermediate portion has a generally elliptical cross-section with a minor diameter no greater than approximately 0.025 inch.

6. The apparatus of claim 1, wherein said motive source comprises a motor.

7. The apparatus of claim 6, wherein said motive source comprises a battery driven motor.

8. The apparatus of claim 1, wherein said coupling connecting the elongated member to the motive source comprises an eccentric.

9. The apparatus of claim 1 wherein said intermediate portion has a cross-section circumscribed by a top, a bottom, and respective sides, and wherein said bottom converges to a point.

10. The apparatus of claim 1, wherein at least a portion of one of said intermediate portion and said tip are impregnated with a diffusant.

11. The apparatus of claim 1, wherein at least a portion of one of said intermediate portion and said tip are impregnated with a medicament.

12. The apparatus of claim 11, wherein said medicament is chosen from the group consisting of fluoride, fluoride releases, germicides, and anti-bacterial releases.

13. The apparatus of claim 1, wherein at least a portion of one of said intermediate portion and said tip are impregnated with a flavor.

14. The apparatus of claim 1, wherein said intermediate portion has a cross-section circumscribed by a top, a bottom, and respective sides, with a maximum transverse distance between said sides no greater than approximately 0.025 inch.

15. The apparatus of claim 1, wherein said coupling is detachably connected to said elongated member.

16. The apparatus of claim 15, wherein said coupling includes an aperture configured to receive said elongated member base portion.

17. Apparatus for cleaning the surfaces of teeth underlying the inter-dental papilla portion of the gums in a human mouth by effecting a flossing action, comprising:

a flexible, resilient elongated member;

said elongated member including a base portion, an elongated intermediate portion of predetermined cross-sectional configuration, and a tip;

said intermediate portion and said tip being capable of being received between adjacent teeth without traversing any contact areas between the teeth from at least the front of the mouth and being capable of effecting the flossing action therebetween; and at least the intermediate portion being capable of being received in the sulcus between a tooth and the adjacent inter-dental papilla portion of the gum for effecting the flossing action therein; and a motive source; and a coupling connecting the base portion of the elongated member to the motive source to effect motion of the elongated member;

said coupling comprising means for effecting a motion of the elongated member having a rotational component.

18. Apparatus for cleaning the surfaces of teeth underlying the inter-dental papilla portion of the gums in a human mouth by effecting a flossing action, comprising:

a flexible, resilient elongated member;

said elongated member including a base portion, an elongated intermediate portion of predetermined cross-sectional configuration, and a tip;

said intermediate portion and said tip being capable of being received between adjacent teeth without traversing any contact areas between the teeth from at least the front of the mouth and being capable of effecting the flossing action therebetween; and at least the intermediate portion being capable of being received in the sulcus between a tooth and the adjacent inter-dental papilla portion of the gum for effecting the flossing action therein; and a motor, said motor including a shaft with an eccentric member mounted thereon;

a coupling connecting the base portion of the elongated member to the motor to effect motion of the elongated member;

said coupling comprising a translation member connected at a first end to said elongated member, and an aperture in the vicinity of the opposing end;

the translation member being pivotally mounted and disposed to receive the eccentric member in said aperture, such that rotation of said eccentric member causes repetitive translation of said first end to effect oscillation of said elongated member.

19. The apparatus of claim 18, wherein said translation member first end includes means for releasably receiving the base portion of said elongated member.

20. The apparatus of claim 19, wherein said means for releasably receiving the base portion of said elongated member comprises an aperture configured to receive said elongated member base portion.

21. The apparatus of claim 20, wherein said intermediate portion has a generally circular cross-section.

22. The apparatus of claim 20, wherein said intermediate portion has a generally elliptical cross-section.

23. The apparatus of claim 18, wherein said intermediate portion has a cross-section circumscribed by a top, a bottom, and respective sides, and at least said sides are arcuate.

24. The apparatus of claim 23, wherein said arcuate sides are each inwardly directed concave.

25. The apparatus of claim 24, wherein said intermediate portion cross-section has a maximum transverse distance between corresponding points on said sides no greater than approximately 0.025 inch.

26. The apparatus of claim 23, wherein said bottom converges to a point.

27. Apparatus for cleaning the surfaces of teeth underlying the interdental papilla portion of the gums in a human mouth, comprising:

a flexible, resilient elongated member having a conduit;
said elongated member including a base portion, an elongated intermediate portion of predetermined cross-sectional configuration, and a tip;
said intermediate portion and said tip being capable of being received between adjacent teeth without traversing any contact areas between the teeth from at least the front of the mouth; and
at least the intermediate portion being capable of being received in the sulcus between a tooth and the adjacent interdental papilla portion of the gum;
a motive source;
a coupling connecting the base portion of the elongated member to the motive source to effect motion of the elongated member;
a fluid reservoir communicating with said elongated member conduit; and
a pump disposed to propel fluid from said reservoir through said conduit.

28. The apparatus of claim 27 wherein said coupling is detachably connected to said elongated member.

29. The apparatus of claim 27, wherein said fluid reservoir is removably coupled to said elongated member conduit.

30. The apparatus of claim 27, wherein said motive source, coupling, pump and reservoir are contained within a common casing.

31. The apparatus of claim 27, wherein said conduit comprises an axial passage through said elongated member communicating with at least one orifice in the surface of said elongated member.

32. The apparatus of claim 27, wherein said intermediate portion has a cross-section circumscribed by a top, a bottom, and respective sides, and said conduit comprises an axial passage through said elongated member communicating with at least one orifice in a side of said elongated member.

33. The apparatus of claim 27, wherein said coupling includes a passage which receives said elongated member and communicates with said elongated member conduit and said reservoir.

34. The apparatus of claim 27, wherein said coupling passage is configured to releasably receive said elongated member base.

35. The apparatus of claim 27, wherein said pump comprises an eccentric element driven by said motive source.

36. The apparatus of claim 27, wherein said motive source, coupling, pump and reservoir are contained within a common casing.

37. The apparatus of claim 36, wherein said reservoir communicates with said elongated member conduit through an elastic tube, and said eccentric element is disposed to cooperate with said tube to create a flow of fluid therethrough.

38. Apparatus for interacting with the surfaces of teeth underlying the inter-dental papilla portion of the gums in a human mouth to effect a flossing action, comprising:

a housing;
a flexible, resilient elongated, non-abrasive member, extending outwardly from one end of said housing;
said elongated member including a base portion, an elongated intermediate portion of predetermined cross-sectional configuration, and a tip;
said intermediate portion and said tip being capable of being received between adjacent teeth from at least the front of the mouth and being capable of effecting the flossing action therebetween; and
at least the intermediate portion being capable of being received in the sulcus between a tooth and the adjacent inter-dental papilla portion of the gum for effecting the flossing action therein;
a motor disposed within said housing; and
a coupling connecting the elongated member to the motor to effect motion of the elongated member.

39. The apparatus of claim 38, wherein said coupling effects oscillation of the elongated member.

40. Apparatus for interacting with the surfaces of teeth underlying the interdental papilla portion of the gums in a human mouth, comprising:

a housing;
a flexible, resilient elongated member, extending outwardly from one end of said housing;
said elongated member including a base portion, an elongated intermediate portion of predetermined cross-sectional configuration, and a tip;
said intermediate portion and said tip being capable of being received between adjacent teeth from at least the front of the mouth; and
at least the intermediate portion being capable of being received in the sulcus between a tooth and the adjacently interdental papilla portion of the gum;
a motor disposed within said housing, said motor includes a shaft with at least a first eccentric member mounted thereon; and
a coupling connecting the elongated member to the motor to effect motion of the elongated member, said coupling comprising:
a translation member connected at a first end to said elongated member, and an axial aperture on the opposing end;
the translation member being pivotally mounted in said housing and disposed to receive the eccentric member in said aperture, such that rotation of said eccentric member causes repetitive translation of said first end to effect oscillation of said elongated member.

41. The apparatus of claim 40, wherein said translation member first end includes means for releasably receiving the base portion of said elongated member.

42. The apparatus of claim 40, wherein said translation member first end includes an axial bore configured to receive said elongated member base portion.

43. Apparatus for interacting with the surfaces of teeth underlying the interdental papilla portion of the gums in a human mouth, comprising:

a housing;
a flexible, resilient elongated member, extending outwardly from one end of said housing and having a conduit communicating with at least one orifice in the surface of said elongated member;
said elongated member including a base portion, an elongated intermediate portion of predetermined cross-sectional configuration, and a tip;

said intermediate portion and said tip being capable of being received between adjacent teeth from at least the front of the mouth; and at least the intermediate portion being capable of being received in the sulcus between a tooth and the adjacent interdental papilla portion of the gum;

a motor disposed within said housing and having a shaft with at least a first eccentric member mounted thereon;

a coupling connecting the elongated member to the motor to effect motion of the elongated member and comprising a translation member connected at a first end to said elongated member, and an axial aperture on the opposing end;

the translation member being pivotally mounted in said housing and disposed to receive the eccentric member in said aperture, such that rotation of said eccentric member causes repetitive translation of said first end to effect oscillation of said elongated member; and a fluid reservoir communicating with said elongated member conduit; and a pump disposed to propel fluid from said reservoir through said conduit.

44. The apparatus of claim 43, wherein said conduit comprises an axial passage through said elongated member.

45. The apparatus of claim 43, wherein said fluid reservoir is releasably coupled to said pump.

46. The apparatus of claim 43, wherein said fluid reservoir is disposed within said housing.

47. The apparatus of claim 46, wherein said fluid reservoir comprises a disposable container prefilled with fluid.

48. The apparatus of claim 43, wherein said intermediate portion has a cross-section circumscribed by a top, a bottom, and respective sides, and said conduit comprises an axial passage through said elongated member communicating with at least one orifice in the surface of said elongated member.

49. The apparatus of claim 43, wherein said coupling includes a passage which receives said elongated member.

50. The apparatus of claim 49, wherein said coupling passage communicates with both said elongated member conduit and said reservoir.

51. The apparatus of claim 49, wherein said coupling passage releasably receives said elongated member base.

52. The apparatus of claim 43, wherein said pump comprises a second eccentric element driven by said motor.

53. The apparatus of claim 52, wherein said reservoir communicates with said elongated member conduit through an elastic tube and said second eccentric element is disposed to cooperate with said tube to create a flow of fluid therethrough.

54. Apparatus for interacting with the surfaces of teeth underlying the interdental papilla portion of the gums in a human mouth, comprising:

a housing;

a flexible, resilient elongated member, extending outwardly from one end of said housing and having a conduit communicating with at least one orifice in the surface of said elongated member;

said elongated member including a base portion, an elongated intermediate portion of predetermined cross-sectional configuration, and a tip;

said intermediate portion and said tip being capable of being received between adjacent teeth from at least the front of the mouth; and at least the intermediate portion being capable of being received in the sulcus between a tooth and the adjacent interdental papilla portion of the gum;

a motor disposed within said housing;

a coupling connecting the elongated member to the motor to effect motion of the elongated member;

a fluid reservoir communicating with said elongated member conduit; and a pump disposed to propel fluid from said reservoir through said conduit.

55. The apparatus of claim 54, wherein:

said reservoir communicates with said elongated member conduit through an elastic tube; and said pump comprises an eccentric element driven by said motor, disposed to cooperate with said tube to create a flow of fluid therethrough.

56. Apparatus for cleaning the surfaces of teeth underlying the inter-dental papilla portion of the gums in a human mouth by effecting a flossing action, comprising:

a flexible, resilient, non-abrasive elongated member;
said elongated member including a base portion, an elongated intermediate portion of predetermined cross-sectional configuration, and a tip;
said intermediate portion and said tip being capable of being received between adjacent teeth without traversing any contact areas between the teeth from at least the front of the mouth and being capable of effecting the flossing action therebetween; and
at least the intermediate portion being capable of being received in the sulcus between a tooth and the adjacent inter-dental papilla portion of the gum for effecting the flossing action therebetween;

a handle;
a coupling releasably connecting the base portion of the elongated member to the handle; and a motive source disposed within said handle; said coupling connecting the base portion of the elongated member to the motive source to effect motion of the elongated member.

* * * * *